United States Patent
Ábrahám et al.

[19]

[11] Patent Number: 5,774,202
[45] Date of Patent: Jun. 30, 1998

[54] METHOD AND OPTICAL MEANS FOR IMPROVING OR MODIFYING COLOR VISION AND METHOD FOR MAKING SAID OPTICAL MEANS

[75] Inventors: György Ábrahám; Guttfriedné Wenzel, both of Budapest, Hungary; Janos Szappanos, Newfane, Vt.

[73] Assignee: Coloryte Hungary Optikai Kutato, Fejleszto es Gyarto Reszvenytarsasag, Szeged, Hungary

[21] Appl. No.: 596,132

[22] PCT Filed: Aug. 18, 1993

[86] PCT No.: PCT/HU93/00045

§ 371 Date: May 1, 1996

§ 102(e) Date: May 1, 1996

[87] PCT Pub. No.: WO95/05621

PCT Pub. Date: Feb. 23, 1995

[51] Int. Cl.[6] .................................................. G02C 7/02
[52] U.S. Cl. .......................... 351/177; 351/162; 351/163; 351/213; 351/219; 623/6
[58] Field of Search .............................. 351/163, 165, 351/213, 44, 177, 162, 219; 623/6

[56] References Cited

U.S. PATENT DOCUMENTS

| | | | |
|---|---|---|---|
| 3,586,423 | 6/1971 | Zeltzer | 351/246 |
| 3,701,590 | 10/1972 | Zeltzer | 351/246 |
| 3,731,993 | 5/1973 | Piringer | 351/165 |
| 3,877,797 | 4/1975 | Thornton | 351/44 |
| 4,028,105 | 6/1977 | Ono et al. | 430/356 |
| 4,168,339 | 9/1979 | Kerko et al. | 351/163 |
| 4,300,819 | 11/1981 | Taylor | 351/41 |
| 4,783,684 | 11/1988 | Rauh | 355/38 |
| 5,218,386 | 6/1993 | Levien | 351/163 |
| 5,319,472 | 6/1994 | Hill et al. | 358/500 |
| 5,369,453 | 11/1994 | Chen et al. | 351/163 |

FOREIGN PATENT DOCUMENTS

| | | |
|---|---|---|
| 279209 | 2/1970 | Austria . |
| 1958480 | 6/1971 | Germany . |
| WO 90/05321 | 5/1990 | WIPO . |

*Primary Examiner*—Georgia Y. Epps
*Assistant Examiner*—Jordan M. Schwartz
*Attorney, Agent, or Firm*—Young & Thompson

[57] ABSTRACT

A method and optical articles for improving or modifying human color vision by using a color filter with a spectral transmission $\tau(\lambda)$ to compensate for differences between a spectral sensitivity $P^*(\lambda)$, $D^*(\lambda)$, $T^*(\lambda)$ of an eye with impaired color vision and spectral sensitivity $P(\lambda)$, $D(\lambda)$, $T(\lambda)$ of an eye with normal color vision. The optical article may be realized as an eyeglass, a contact lens or an intraocular lens, or by any other optical implement placed between the eye and the object to be viewed.

23 Claims, 8 Drawing Sheets

METHOD AND OPTICAL MEANS FOR IMPROVING OR MODIFYING COLOR VISION AND METHOD FOR MAKING SAID OPTICAL MEANS

TECHNICAL FIELD

The invention relates to a method and means for improving or modifying color vision, and a method for making the optical means.

BACKGROUND ART

The human eye is able to detect electromagnetic radiation in the wavelength range of visible light which extends approx. from 380 nm to 780 nm. The light efficiency of human vision in dependence of wavelength is defined by the so-called visibility curve. In the human eye there are three orthochromatic receptors (pigments) assuring color vision, called protos, which is sensitive to red, deuteros, which is sensitive to green, and tritos, which is sensitive to violet. Sensation of the yellow color is aroused by simultaneous stimuli of the protos and the deuteros. Simultaneous stimuli of the tritos and the deuteros causes the vision of the color turquoise, while simultaneous stimuli of the tritos and the protos leads to the sensation of the color purple. Other transitional shades of colors are produced by simultaneous stimuli of the three receptors with different intensities.

Figure 1:
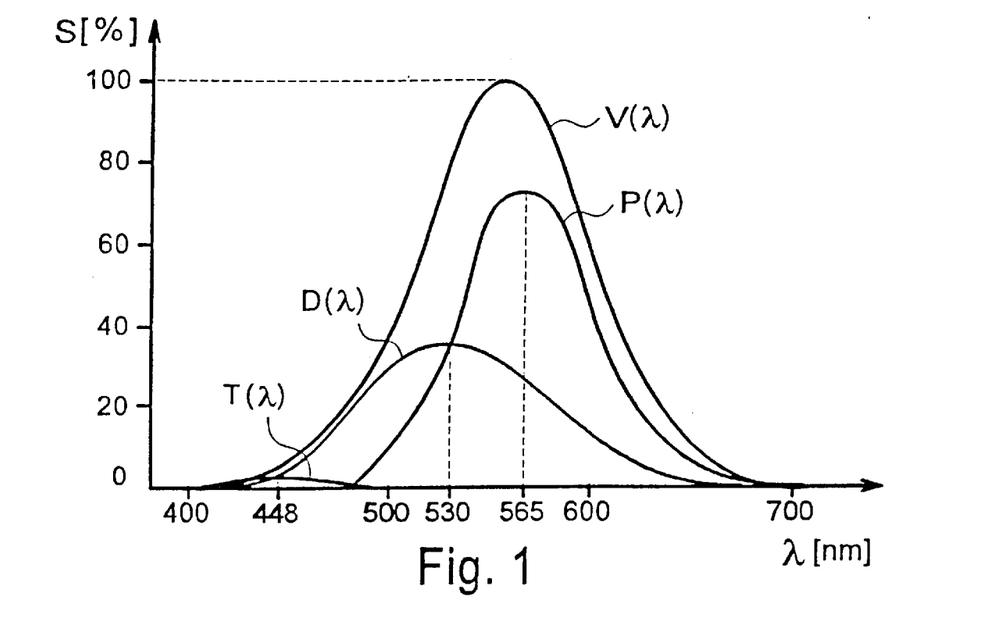
FIG. 1 is a diagram depicting visibility curve of a normal human eye and spectral sensitivity curves of color-sensitive receptors thereof.

Diagrams of spectral sensitivity of the protos, the deuteros and the tritos for people having normal (average) colour vision are well known. FIG. 1 illustrates the visibility curve $V(\lambda)$ for normal human eye and the sensitivity curves $P(\lambda)$, $D(\lambda)$ and $T(\lambda)$ of protos, deuteros and tritos, respectively, for normal human color vision.

The spectral sensitivities of receptors in the eye can be determined by individual measurements (W. B. Marks, W. H. Dobbelle, E. F. Mac Nichol: Visual Pigments of Single Primate Cones, Science, Vol. 143, March 1964). Rushton performed microspectrographic measurements on eyes of living human beings and monkeys (Rushton: Visual Pigments and Color Blindness, Scientific American, March 1975). In the microspectrographic method, a thin monochromatic light beam is imaged on the retina through the pupil of the eye to be tested, the size of the light beam—when reaching the retina—does not exceed that of each receptor (protos, deuteros, tritos). The intensity of the light beam is continuously measured prior to emission and also after being reflected from the receptor. The difference of the two corresponds to the intensity of light absorbed by the given receptor, which is characteristic of the receptor's sensitivity in the given wavelength. By altering the wavelength of the testing light beam, the spectral sensitivity curve of the given receptor can be determined (Leo M. Hurvich: Color Vision, Sinauer Associates Inc., Sunderland, Mass., U.S.A., 1981, pp. 121–122).

There is another method for determining the spectral sensitivity curves of receptors by a mathematical method from results of color mixing measurements (K. Wenzel and G. Szász: Numerical method for determining simultaneous functions having been measured with an indirect measuring method (in Hungarian), Finommechanika-Mikrotechnika, 1985, Vol. 24, No. 8/9, pp. 250–252). Results obtained by this computing method are in agreement with the results of said microspectrographic measurements.

It is well known that people do not have exactly the same color vision. So, e.g. the so-called color blind people see only two basic colors instead of three. If there is a lack of protos receptors, the color blind person is called protanop, in lack of deuteros receptors, we speak about a deuteranop person, and if tritos receptors are missing, the person is called tritanop. Additionally, people with anomalous color vision are also known, and although they have all the three receptors, they see the colors in a different way than normal people. The most frequent form of anomalous color vision appears as red-green parachromatism. People suffering in red-green parachromatism do not recognize pseudoisochromatic tables (known in practice as dotted figures) and they are not able to distinguish between red, yellow and green signals used in traffic control. Different types of parachromatism are described on pages 222 to 269 in the textbook of Leo M. Hurvich quoted above.

Anomalous color vision is an inherited characteristic and it does not change over the life-span of a person, except of color blindness caused by certain diseases and unless the effect is temporarily caused by some poisonous materials, e.g. alcohol. As much as approx. 2.1% of the entire population is color blind (protanopy is approx. 1%, deuteranopy is approx. 1.1% and tritanopy is approx. 0.01%). Approx. 6.3% of the population have anomalous color vision (protanomaly is approx. 1%, deuteranomaly is approx. 5.3% and tritanomaly is approx. 0.01%). This means that about 8.4% of the entire population do not see colors properly. The above data refer to male population of the Caucasian (European) group of people, while for other groups of people and for female population investigations resulted in smaller values.

Generally, color blind persons, or people with parachromatism cannot have a driver licence; they cannot be employed as typographers, industrial designers and electricians; they cannot work in textile, cosmetic and ceramic industries etc. There are more than 100 occupations which are not recommended for persons suffering in parachromatism.

Attempts have already been made to correct the error of color vision by color filters placed in front of the eye. The solutions described in U.S. Pat. Nos. 3,586,423, 3,701,590 and 4,300,819, by using a color lens for one eye and a transparent one for the other, ensure some rough color distinguishing ability for color blind people, however, they do not provide any improvement for people suffering in parachromatism.

In U.S. Pat. No. 3,877,797 an optical filter combination improving the color distinguishing ability was recommended, which filters the light arriving into the eye in two bands, that is in the vicinity of 490 nm and 580 nm.

In WO 90/05321 there is a light filter for improving vision of persons whose lenses are affected by cataract or whose vision is impaired by retina-related conditions. The light filter has a low transmission under 450 nm and a much higher transmission over 450 nm. Practically, the filter is a yellow filter. The rise of the transmission curve at 450 nm shall be as steep as possible. This light filter is not suitable to compensate parachromatism, in fact, it deteriorates normal color vision in order to improve visual acuity and contrast sensitivity, respectively.

In U.S. Pat. No. 5,218,386 eye-glasses for altering color perception are described. A first optical filter, worn over the left eye, selectively passes light in three bands corresponding to red, green and blue. A second optical filter, worn over the right eye, selectively passes light in complementary portions of the wavelength bands of the first optical filter. In this manner, as the two eyes see different colors of the same scene and the received colors are integrated in the human brain, an artificial color perception with increased color vividness can be obtained. This can be used e.g. for detecting forgery in writings or in the inspection of artworks. However, these eye-glasses cannot help for people suffering in parachromatism. In U.S. Pat. No. 3,731,993 a color filter was proposed for correcting parachromatism. The filter includes color filter components placed as a mosaic side by side corresponding to the three basic colors (red, green, blue). The spectral transmission factor of each set of color filter components is inversely proportional with the corresponding color sensitivity of a person with anomalous colour vision.

DE-OS 1,958,480 relates to an apparatus and a method for compensating parachromatism which is measured by establishing saturation grade of red, green and blue colors, respectively, at a perception point of the eye tested. An optical filter is proposed to correct parachromatism which optical filter attenuates transmitting light in at least one of the wavelength ranges of red, green and blue in order to compensate the deviation in the number of any type of color-sensitive receptors with respect to normal vision. E.g. if there is too few red receptors, transmitting light shall be attenuated in the wavelength ranges of green and blue, or if there is too much green receptors, a proportionate attenuation shall take place in the wavelength range of green. This solution is based on the assumption that the parachromatism is due to an abnormal relation in numbers of color-sensitive receptors in the eye and, therefore, a correction of the parachromatism may be achieved if, by attenuation of the intensity of transmitted light in the red, green and/or blue wavelength ranges, a proper relation between intensities of stimuli of color-sensitive-receptors is ensured.

These solutions, by diminishing the light intensity in some range of the spectrum through filtering, only achieve the result of virtually reducing amplitudes of the spectral sensitivity curve of some of the color-sensitive receptors, but, according to experiences, are not suitable for correcting parachromatism for a large number of persons with anomalous color vision. Until now, there is no implement on the market that would be able to correct parachromatism in most cases.

DISCLOSURE OF INVENTION

By creating the invention, it has been intended to find a solution for correcting parachromatism. Thus, a first objective is to provide a method by which anomalous color vision could be corrected. A second objective is to provide means suitable to improve or modify color vision.

In most cases parachromatism is caused by the fact that spectral sensitivity curves of receptors of an eye with anomalous color vision are different from the corresponding sensitivity of an eye with normal color vision. As to parachromatism we have discovered that sensitivity curves of such an eye may be displaced along the wavelength independently from each other and in both directions with respect to the corresponding sensitivity curves of an eye with normal color vision, and further, that there may also be some differences in the shape of the sensitivity curves. Therefore, spectral sensitivity curves of protos, deuteros and tritos receptors of an eye with anomalous color vision must be analysed separately for determining the type and extent of parachromatism in order to improve it.

We have further recognized that displacements of sensitivity curves of the receptors can be corrected by appropriately selected color filters as, in most cases of parachromatism, the displacement of any sensitivity curve along the wavelength is of an extent that an inevitable reduction in light intensity caused by the color filter used can largely be compensated for each type of receptors by the adaptation of the human eye. E.g. the application of a color filter with a transmission of 10% causes a very little reduction in light perception owing to the logarithmic sensing characteristics of the eye.

We have also recognized that, by using special color filters according to the invention, any person having normal or anomalous color vision can be endowed with a special color vision and, in such a manner, his color distinguishing ability can be increased for special purposes, e.g. for recognition of plant parasites, treating of foodstuffs and pharmaceutical products, detection of counterfeits, etc.

Thus, on the one hand, the invention is a method for improving or modifying color vision of an eye, comprising determining the color vision of the eye and modifying the color vision by applying a color filter. According to the invention, the method is characterized by determining spectral sensitivity curves, or wavelength values associated with maxima of said spectral sensitivity curves, of color-sensitive receptors of the eye with color vision to be modified, and applying the color filter with a spectral transmission so that it compensates, in at least one of three wavelength ranges around maximum values of spectral sensitivity curves of color-sensitive receptors, displacements of the spectral sensitivity curves along the wavelength, as determined, with respect to corresponding spectral sensitivity curves of receptors of an eye with normal or desired color vision.

On the other hand, the invention relates to optical means for improving or modifying color vision of an eye, comprising a color filter which has a spectral transmission so that it compensates, in at least one of three wavelength ranges around maximum values of spectral sensitivity curves of color-sensitive receptors, displacements of the spectral sensitivity curves along the wavelength, as determined, of the eye with color vision to be modified with respect to corresponding spectral sensitivity curves of receptors of an eye with normal or desired color vision.

Preferred embodiments of the present invention are described in dependent claims attached to this specification.

It is an advantage of the invention that it allows eliminating or reducing parachromatism, which has been impossible so far, by optical means that are relatively simple, can be produced by technology per se known in optics, and are suitable for applying in ophthalmologic practice.

It is a further advantage that by the use of the invention not only parachromatism can be eliminated, but a color vision, being more selective in some respect than the vision of a normal eye, can also be assured.

BRIEF DESCRIPTION OF THE DRAWINGS

Hereinafter, the invention will be described by means of preferred embodiments shown in the drawings, where.

MODES FOR CARRYING OUT THE INVENTION

In the figures identical elements or element of identical functions are marked by same reference signs.

FIG. 1 depicts a visibility curve $V(\lambda)$ showing spectral light efficiency of a normal human eye, and spectral $P(\lambda)$, $D(\lambda)$, $T(\lambda)$ sensitivity curves of light sensitive receptors in a normal human eye, where on the vertical axis the relative spectral sensitivity $S(\lambda)$ in % and on the horizontal axis the wavelength $\lambda$ in nm are shown. The visibility curve $V(\lambda)$ is a resultant of the sensitivity curves $P(\lambda)$, $D(\lambda)$, and $T(\lambda)$. It can be seen that the protos sensitivity curve $P(\lambda)$ has a maximum at approx. 565 nm, the deuteros sensitivity curve $D(\lambda)$ has a maximum at approx. 530 nm and the tritos sensitivity curve $T(\lambda)$ has a maximum at approx. 448 nm.

Figure 2:
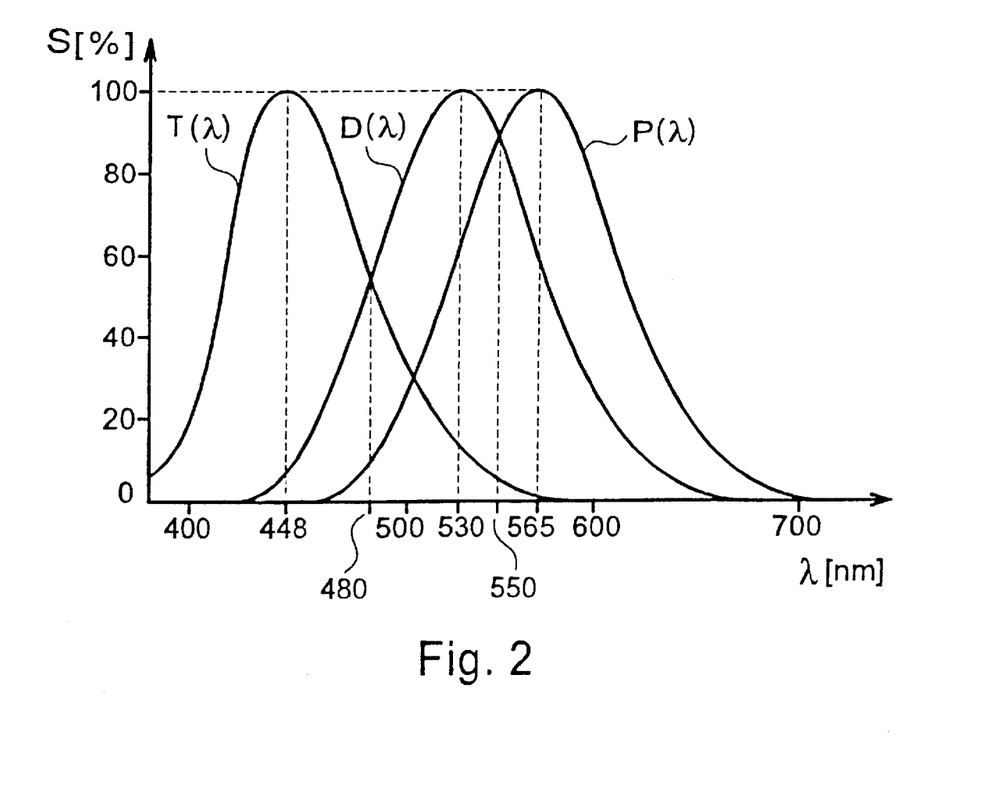
FIG. 2 is a diagram depicting normalized spectral sensitivity curves of color-sensitive receptors of a normal human eye.

In FIG. 2 normalized spectral sensitivity curves $P(\lambda)$, $D(\lambda)$, $T(\lambda)$ of light sensitive receptors in a normal human eye are shown, where on the vertical axis the relative spectral sensitivity $S(\lambda)$ in % and on the horizontal axis the wavelength $\lambda$ in nm is depicted. In the diagrams shown in FIGS. 3 and 9, also the normalized spectral sensitivity curves are shown. The intersection point of the normalized sensitivity curves $T(\lambda)$ and $D(\lambda)$ is approx. at 480 nm and that of the normalized sensitivity curves $D(\lambda)$ and $P(\lambda)$ is approx. at 550 nm. The maximum and intersection points and to a certain extent the shapes of the sensitivity curves may be different for each group of people.

In the course of our experiments we have recognized that the most frequent reason for anomalous color vision is the deviation of the sensitivity curves of the receptors from the sensitivity curves of the corresponding receptors in a normal eye. This recognition led us to compare sensitivity curves $P^*(\lambda)$, $D^*(\lambda)$ and $T^*(\lambda)$ of an eye to be tested with respective sensitivity curves $P(\lambda)$, $D(\lambda)$ and $T(\lambda)$ of a normal eye separately. In the course of examination of persons with anomalous color vision, we have found that the sensitivity curves of the receptors may be displaced independently of each other and in both directions along the wavelength axis. We have also experienced that a deviation could be found in the shape of each curve, e.g. the curve is wider or narrower than the corresponding curve of a normal eye. The displacement along the wavelength and the deviation in shape could occur simultaneously. According to the invention the following method is used for correcting parachromatisin or for modifying color vision.

First of all, spectral sensitivity curves $P^*(\lambda)$, $D^*(\lambda)$ and $T^*(\lambda)$ of the tested eye will be determined, e.g. by a per se known microspectrographic measurement. Then, the color vision of the tested eye is modified by the application of a color filter, i.e. practically the corresponding sensitivity curves $P^*(\lambda)$, $D^*(\lambda)$ and $T^*(\lambda)$ are corrected so that the color sensing of protos, deuteros and tritos receptors in the tested eye correspond to the protos, deuteros and tritos spectral sensitivity curves $P(\lambda)$, $D(\lambda)$, and $T(\lambda)$ of a human eye-with normal or desired color vision.

The spectral transmission characteristic $\tau(\lambda)$ of the color filter for the above correction may be determined on the basis of the following equations:

$$P(\lambda)=P^*(\lambda)\cdot\tau_P(\lambda) \qquad (1)$$

$$D(\lambda)=D^*(\lambda)\cdot\tau_D(\lambda) \qquad (2)$$

$$T(\lambda)=T^*(\lambda)\cdot\tau_T(\lambda), \qquad (3)$$

where $P(\lambda)$, $D(\lambda)$ and $T(\lambda)$ are sensitivity curves of protos, deuteros and tritos receptors of a human eye with normal or desired color vision, $P^*(\lambda)$, $D^*(\lambda)$ and $T^*(\lambda)$ are sensitivity curves of protos, deuteros and tritos receptors of the eye with color vision to be modified, and $\tau_P(\lambda)$, $\tau_D(\lambda)$ and $\tau_T(\lambda)$ are spectral transmission characteristics of color filters for sensitivity corrections of protos, deuteros and tritos receptors.

From the equations (1) to (3), the transmission characteristics $\tau_P(\lambda)$, $\tau_D(\lambda)$ and $\tau_T(\lambda)$ are obtained as the following quotient functions:

$$\tau_P(\lambda) = \frac{P(\lambda)}{P^*(\lambda)} \qquad (4)$$

$$\tau_D(\lambda) = \frac{D(\lambda)}{D^*(\lambda)} \qquad (5)$$

$$\tau_T(\lambda) = \frac{T(\lambda)}{T^*(\lambda)}. \qquad (6)$$

The transmission characteristic $\tau(\lambda)$ of a single color filter correcting all receptor errors is determined on basis of the transmission characteristics $\tau_P(\lambda)$, $\tau_D(\lambda)$ and $\tau_T(\lambda)$ according to equations (4) to (6), substantially as a resultant thereof. In determining the resultant, sensitivity curves $P(\lambda)$, $D(\lambda)$ and $T(\lambda)$ of the receptors in a normal human eye, as shown in FIG. 2, are taken as a basis. The transmission characteristic $\tau_P(\lambda)$ is chosen in a first wavelength range around maximum value of spectral sensitivity curve $P(\lambda)$ of protos, the transmission characteristic $\tau_D(\lambda)$ in a second wavelength range around maximum value of spectral sensitivity curve $D(\lambda)$ of deuteros, and the transmission characteristic $\tau_T(\lambda)$ in a third wavelength range around maximum value of spectral sensitivity curve $T(\lambda)$ of tritos, of a human eye with normal color vision.

Boundary values of said three wavelength ranges can be fixed according to intersection points of normalized sensitivity curves $P(\lambda)$, $D(\lambda)$ and $T(\lambda)$ of a normal human eye. So the first wavelength range extends from a first wavelength value, namely 550 nm, corresponding to the intersection point of sensitivity curves $P(\lambda)$ and $D(\lambda)$ to 780 nm, the second wavelength range extends from a second wavelength value, namely 480 nm, corresponding to the intersection point of sensitivity curves $D(\lambda)$ and $T(\lambda)$ to said first wavelength value, and the third wavelength range extends from 380 nm to said second wavelength value. The boundary values of the three wavelength ranges can also be fixed according to maxima of sensitivity curves $P(\lambda)$, $D(\lambda)$ and $T(\lambda)$ of a normal human eye so that the boundary values are at midpoints between wavelength values at the maxima. In this way, said first and second wavelength values are 548 nm and 489 nm, respectively. In practice, the first and second wavelength values can be chosen within ranges 550±30 nm and 480±20, respectively.

However, the curve consisting of three sections so obtained generally does not represent a continuous function, discontinuities may occur at the boundaries of wavelength ranges. According to the invention, the transmission characteristic $\tau(\lambda)$ can be derived from the curve in different ways. In a first method, a continuous curve is matched to the three sections as far as technically possible. Hence, at discontinuities between sections the continuous curve passes from one section into the adjacent section on a path as short as possible. In another method, a continuous curve is derived by eliminating the discontinuities by multiplying the sections by constants. The constant can be determined e.g. by dividing the higher value by the lower value at each discontinuities, and multiplying each value of the section associated with the lower value by the constant so obtained. Breakpoints in the continuous curve, which might occur at the boundaries of the wavelength ranges, are rounded off in the course of practical realization. According to a further method, by multiplying the sections by constants, the constants are determined so that the decrease of light intensity in particular wavelength range caused by the color filter, which decrease would exceed the adaptation ability of the eye, is reduced. In this case, a continuous curve is obtained by approximating a curve to the three sections multiplied by constants.

The continuous curve so obtained is normalized in order that the color filter has the lowest possible light absorption. For an optimal normalization each value of the continuous curve is divided by the maximum value and multiplied by 100 within the wavelength range (380–780 nm) of visible light. Preferably, the normalization shall be made to at least 90%. After the normalization the transmission characteristic $\tau(\lambda)$ to be realized is obtained.

The light absorption caused by the color filter of transmission characteristic $\tau(\lambda)$ is compensated for each receptor within certain limits by the adaptation ability of the eye. Because of the eye's higher sensitivity caused by the adaptation, it is advisable to coat the optical means according to the invention with a protecting layer per se known, providing protection for the eye against UV radiation.

Figure 3:
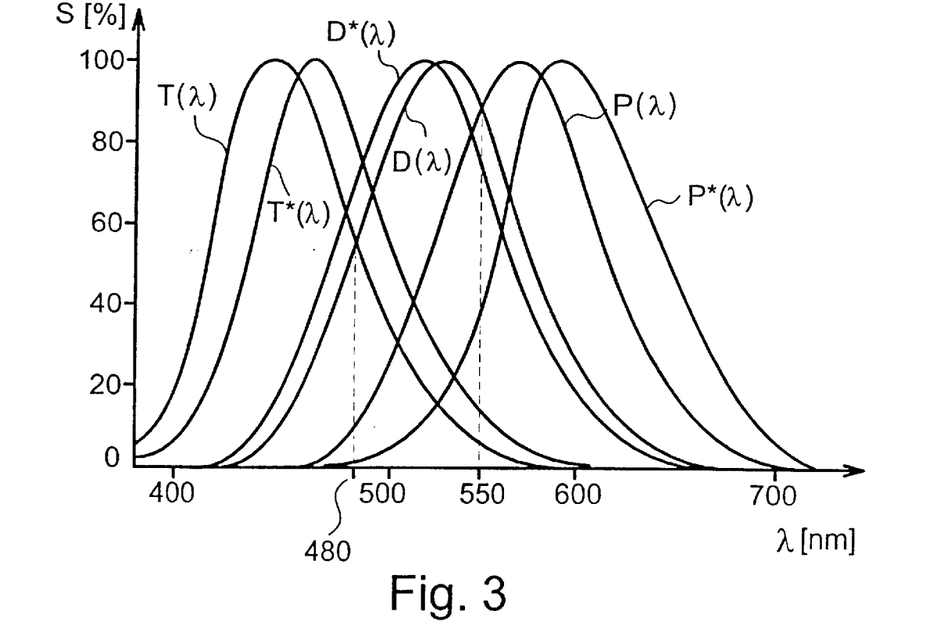
FIG. 3 is a diagram showing spectral sensitivity, curves of color-sensitive receptors of a normal human eye and those of a human eye exhibiting color vision anomaly.

FIG. 3 depicts sensitivity curves $P(\lambda)$, $D(\lambda)$, $T(\lambda)$ of color sensitive receptors in a normal human eye, and sensitivity curves $P^*(\lambda)$, $D^*(\lambda)$, $T^*(\lambda)$ of corresponding receptors in an eye with anomalous color vision. The sensitivity curve $P^*(\lambda)$ is displaced in the direction of greater wavelengths in comparison to sensitivity curve $P(\lambda)$ and its shape also deviates from that of sensitivity curve $P(\lambda)$. The sensitivity curve $D^*(\lambda)$ is displaced in the direction of smaller wavelengths in comparison to sensitivity curve $D(\lambda)$ and its shape is practically the same as that of sensitivity curve $D(\lambda)$. Further, sensitivity curve $T^*(\lambda)$ is displaced in the direction of greater wavelengths in comparison to sensitivity curve $T(\lambda)$ and its shape is also different from that of sensitivity curve $T(\lambda)$. The extents of the displacements are as follows: $\Delta\lambda_P$=17.5 nm, $\Delta\lambda_D$=−4 nm, $\Delta\lambda_T$=17.5 nm.

Figure 4:
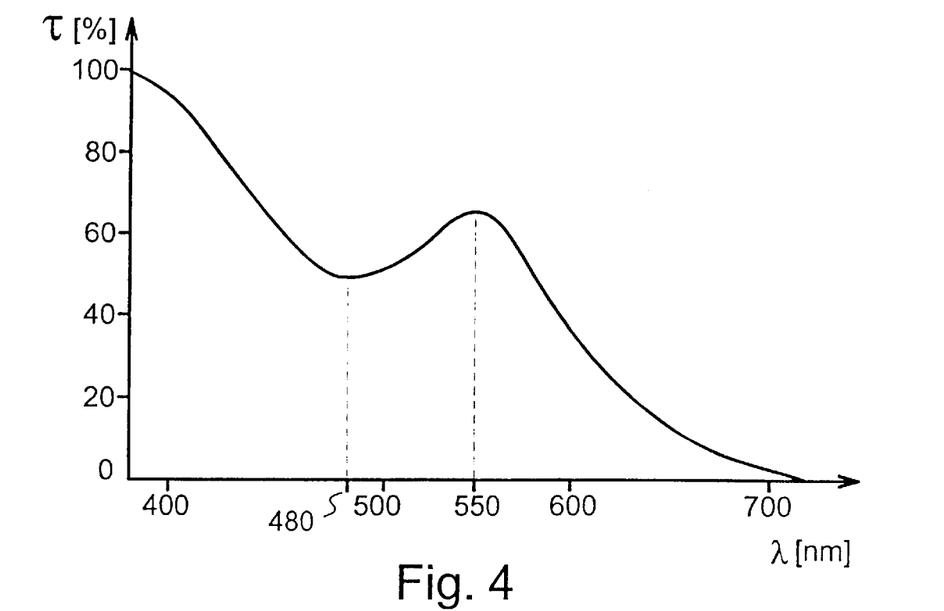
FIG. 4 is a diagram showing spectral transmission characteristic of a color filter according to the invention for improving the color vision of an eye exhibiting the anomaly as of FIG. 3.

FIG. 4 shows spectral transmission characteristic $\tau(\lambda)$ as a function of wavelength $\lambda$ of a color filter correcting the parachromatism as per FIG. 3. It can be seen that the transmission characteristic $\tau(\lambda)$ has a monotonously decreasing transmission in the wavelength range around the maximum value of the sensitivity curve $T(\lambda)$, while the transmission monotonously increases in the wavelength range around the maximum value of the sensitivity curve $D(\lambda)$, and again monotonously decreases in the wavelength range around the maximum value of the sensitivity curve $P(\lambda)$. The color vision of the eye with the parachromatism is influenced by this color filter so as if the sensitivity curve $T^*(\lambda)$ shown in FIG. 3 would be virtually shifted to the left by $\Delta\lambda_T$, the sensitivity curve $D^*(\lambda)$ to the right by $\Delta\lambda_D$ and the sensitivity curve $P^*(\lambda)$ also to the left by $\Delta\lambda$P. In practice, the transmission characteristic $\tau(\lambda)$ is rounded off at the boundaries of the wavelength ranges.

If the spectral sensitivity curves $P^*(\lambda)$, $D^*(\lambda)$, $T^*(\lambda)$ of the tested eye are practically of the same shape as the spectral sensitivity curves $P(\lambda)$, $D(\lambda)$, $T(\lambda)$ of an eye with normal color vision, and there is only a displacement in the direction of longer or shorter wavelengths at one sensitivity curve, or at two or even at all the three sensitivity curves individually, a color filter can be applied, the transmission characteristic $\tau(\lambda)$ of which, in each of said three wavelength ranges around maximum values of sensitivity curves $P(\lambda)$, $D(\lambda)$ and $T(\lambda)$ of an eye with normal color vision, is monotonously increasing thereby causing a virtual shift of the sensitivity curve in the direction of greater wavelengths, or monotonously decreasing thereby causing a virtual shift in the direction of smaller wavelength, or of a substantially constant value causing practically no virtual shift along the wavelength. In such cases, it is enough to determine the displacements of maximum values of the sensitivity curves $P^*(\lambda)$, $D^*(\lambda)$ and $T^*(\lambda)$ of the tested eye for establishing the transmission characteristic $\tau(\lambda)$ of the color filter in each of the three wavelength ranges.

The transmission characteristic $\tau(\lambda)$ of the color filter providing the virtual shifts along the wavelength can be obtained by generating three quotient curves from spectral sensitivity curves $P(\lambda)$, $D(\lambda)$ and $T(\lambda)$ of a human eye with normal or desired color vision and curves obtained by shifting maxima of these spectral sensitivity curves to maxima, as determined, of corresponding spectral sensitivity curves $P^*(\lambda)$, $D^*(\lambda)$ and $T^*(\lambda)$ of the eye with color vision to be modified, and choosing the spectral transmission in each of the three wavelength ranges substantially according to the respective quotient curve.

Figure 5:
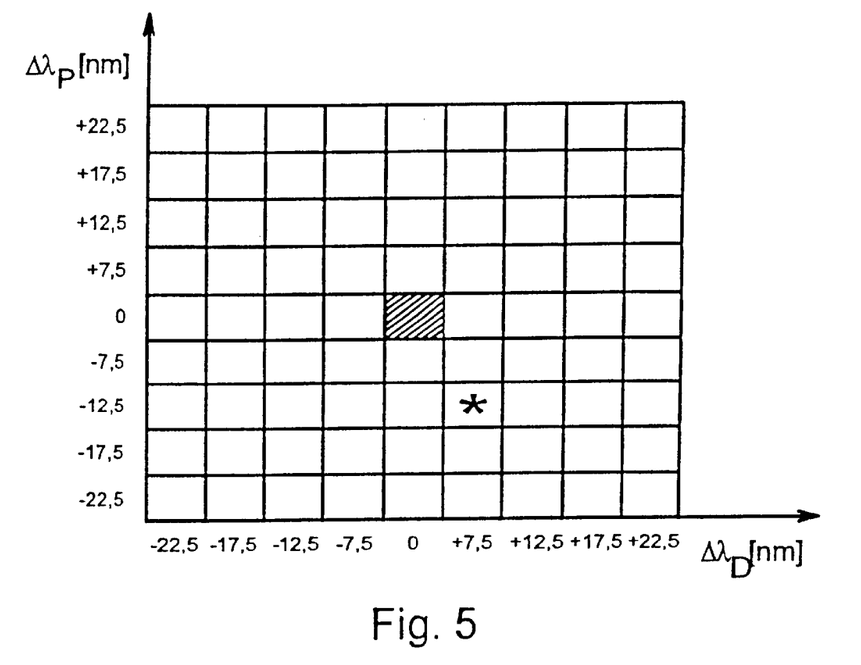
FIG. 5 is a diagram depicting wavelength shifts of a set of lenses comprising color filters according to the invention.

It has been found that a majority of the eyes with anomalous color vision exhibit only displacements along the wavelength as mentioned above, and in most cases of parachromatism there are displacements at sensitivity curves $P^*(\lambda)$ and $D^*(\lambda)$, only. For a correction of such anomalous color vision, according to the invention, pre-manufactured set of eye-glasses or contact lenses can be used, similarly to known sets of dioptric lenses. Members of such set represent a two-dimensional multitude, as shown in FIG. 5, and are fitted with color filters that ensure virtual shifts of the sensitivity curves along the wavelength in the wavelength ranges around maximum values of spectral sensitivity curves $P(\lambda)$ and $D(\lambda)$ of a human eye with normal color vision according to coordinate values $\Delta\lambda_P$ and $\Delta\lambda_D$, respectively, of FIG. 5. The $\Delta\lambda_P$ and $\Delta\lambda_D$ coordinate values are changing incrementally, preferably in steps of 5 nm. If a displacement of tritos sensitivity curve $T^*(\lambda)$ is also taken into account, these cases are of lesser importance in parachromatism, the set represents a three-dimensional multitude.

As shown in FIG. 5, $\Delta\lambda_D$ on the horizontal axis and $\Delta\lambda_P$ on the vertical axis may have values of 0, ±7.5, ±12.5, ±17.5 and ±22.5 nm. If the sensitivity curve $D^*(\lambda)$ of an eye with color vision to be corrected is displaced e.g. by 6 nm towards greater wavelength and the sensitivity curve $P^*(\lambda)$ of the same eye is displaced e.g. by 12 nm towards smaller wavelengths, then a member of the set, marked by an asterisk in FIG. 5, is selected for the correction. This member provides for the sensitivity curve $D^*(\lambda)$ a virtual shift of 7.5 nm towards smaller wavelengths in the wavelength range around the maximum sensitivity of deuteros and for the sensitivity curve $P^*(\lambda)$ a virtual shift of 12.5 nm towards greater wavelengths, in the wavelength range around the maximum sensitivity of protos, which, in practice, ensures an appropriate correction of this parachromatism.

The optical means improving or modifying color vision according to the invention can be implemented in many ways. A color filters with a desired transmission characteristic $\tau(\lambda)$ can be advantageously realized by per se known interference filters consisting of optical thin-layers. By means of interference filters, a color filter of almost any transmission characteristic $\tau(\lambda)$ can be made. In this technology numerous thin-layers of different materials and thicknesses falling into the $\mu$m range are applied on glass or plastic carrier. The thicknesses and materials of the layers can be designed by computer programs commercially available. As input data for the design, it is sufficient to specify the transmission characteristic $\tau(\lambda)$ of the color filter to be implemented.

In some cases, the color filter may be made from colored glass or plastic of appropriate transmission, or from the combination of such colored glass or plastic layers. In the literature and in glass catalogs spectral transmissions of numerous colored glasses are described (e.g. Van Fanderlik: Optical Properties of Glass, Elsevier, Amsterdam, 1983, pp. 154–155).

The color filter according to the invention may also be implemented by a glass or plastic carrier having on its surface one or more dye layers of appropriate transmission. By eye-glass painting procedures usually applied in the optical industry, water- or alcohol-based solutions of aniline dyes with various spectral transmission can be applied on a lens surface. An appropriate transmission $\tau(\lambda)$ can be assured by subtractive mixing of various dyes, i.e. by an appropriate selection of material composition and thickness of dye layers applied. The painting can be conserved by a protecting thin $SiO_2$ layer.

The color filter according to the invention may also be realized by a combination of the technologies mentioned above. E.g. it is possible to ensure a required transmission through joint use of colored glass and dye on its surface. The interference filter may be combined with colored glass, so that the optical thin-layers are applied on a colored carrier.

In the following some examples will be given for color filters used in optical means according to the invention.

EXAMPLE 1

Figure 6:
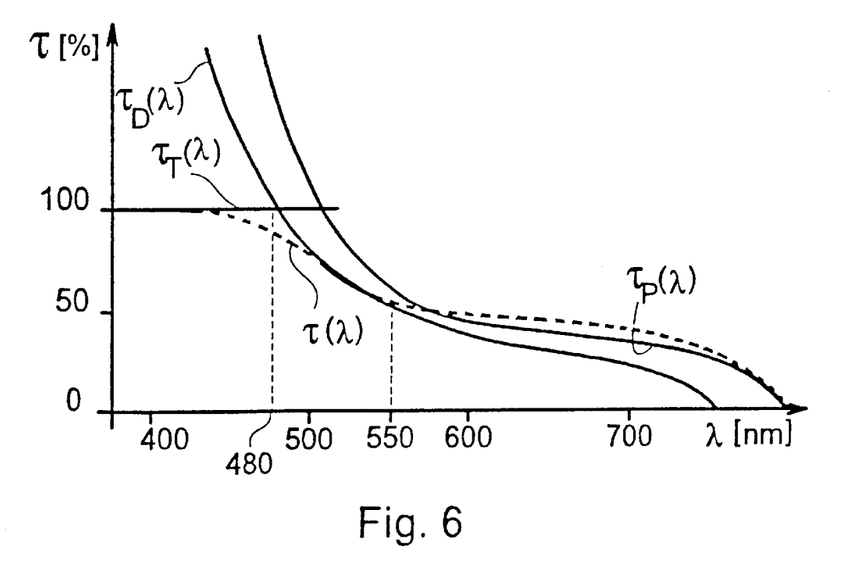
FIGS. 6 to 8 are diagrams showing spectral transmission characteristics of color filters according to the invention for applying in further cases of anomalous color vision.

By testing a given person's eye, it has been determined that each of the sensitivity curves of the protos and deuteros was displaced by 17.5 nm towards greater wavelengths, while the tritos receptors were of a sensitivity corresponding to that of a normal eye. This means that $\Delta\lambda_P$=17.5 nm, $\Delta\lambda_D$=17.5 nm and $\Delta\lambda_T$=0. For protos correction a color filter of transmission characteristic $\tau_P(\lambda)$ as shown in FIG. 6 would be necessary, while for deuteros correction a color filter of transmission characteristic $\tau_D(\lambda)$ also shown would be required. For tritos no correction is necessary, and this corresponds to a horizontal transmission characteristics $\tau_T(\lambda)$. The transmission characteristics $\tau_P(\lambda)$ and $\tau_D(\lambda)$ are obtained according to equations (4) and (5), respectively. The transmission characteristic $\tau(\lambda)$ to be implemented, as shown by dotted line in FIG. 6, is generated so that the transmission characteristics $\tau_P(\lambda)$, $\tau_D(\lambda)$ and $\tau_T(\lambda)$ are chosen in the wavelength ranges from 550 to 780 nm, from 480 to 550 nm, and from 380 to 480 nm, respectively, and these three sections are multiplied by constants in order to obtain a continuous curve. The color filter can be implemented by applying optical layers of specified materials and thicknesses on a carrier by means of any thin-layer technology, e.g. by vaporizaton. To obtain the transmission characteristic $\tau(\lambda)$ as shown, the following twelve thin-layers are applied in sequence on a glass carrier.

| Layer 1  | 0.12 $\mu$m | $MgF_2$ |
|----------|-------------|---------|
| Layer 2  | 0.75 $\mu$m | $SiO_2$ |
| Layer 3  | 0.25 $\mu$m | $ZrO_2$ |
| Layer 4  | 0.25 $\mu$m | $SiO_2$ |
| Layer 5  | 0.25 $\mu$m | $ZrO_2$ |
| Layer 6  | 0.25 $\mu$m | $SiO_2$ |
| Layer 7  | 0.25 $\mu$m | $ZrO_2$ |
| Layer 8  | 0.25 $\mu$m | $SiO_2$ |
| Layer 9  | 0.25 $\mu$m | $ZrO_2$ |
| Layer 10 | 0.25 $\mu$m | $SiO_2$ |
| Layer 11 | 0.30 $\mu$m | $ZrO_2$ |
| Layer 12 | 0.15 $\mu$m | $SiO_2$ |

As a thirteenth layer, a UV-protecting layer per se known can be applied. As a carrier, e.g. a +2D eye-glass is used, if the person uses this eye-glass on his tested eye. If he does not wear glasses, the layers are applied on a 0D eye-glass.

EXAMPLE 2

Figure 7:
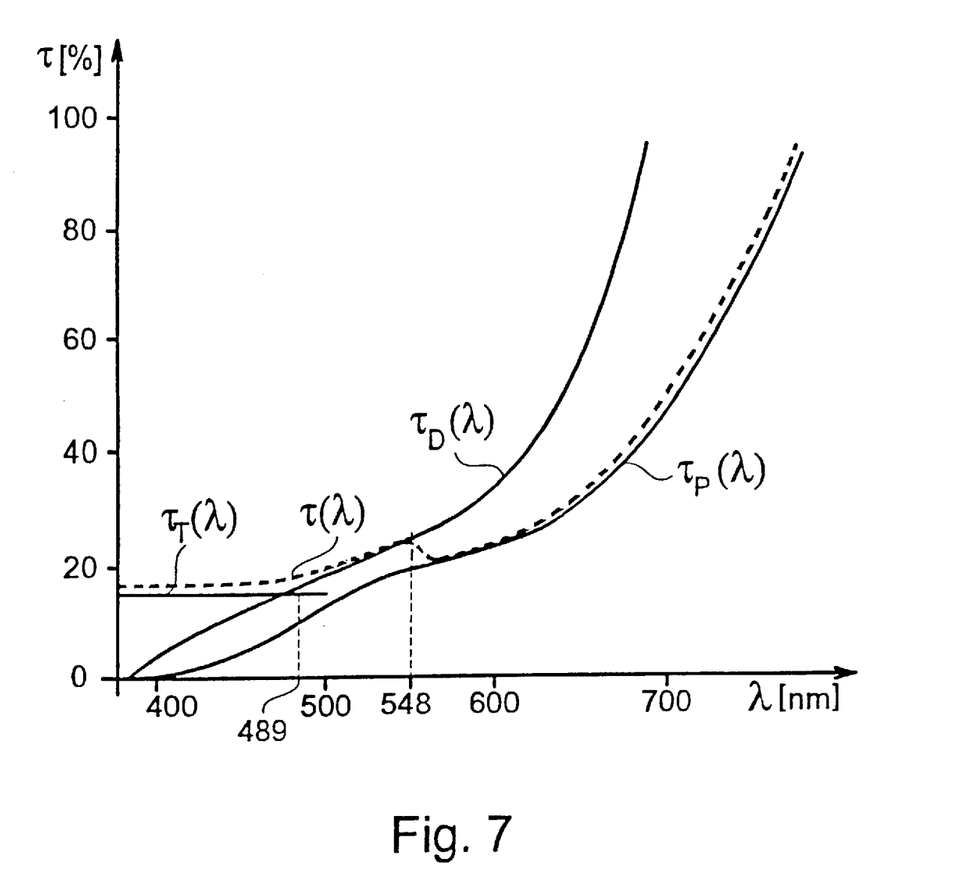

The sensitivity curves of protos and deuteros of the tested person's eye were displaced towards smaller wavelengths by 27.5 nm and 17.5 nm, respectively, while the tritos receptors had a sensitivity corresponding to that of a normal eye. This means that $\Delta\lambda_P$=−27.5 nm, $\Delta\lambda_D$=−17.5 nm and $\Delta\lambda_T$=0. For protos correction a color filter of transmission characteristic $\tau_P(\lambda)$ as shown in FIG. 7 would be required, while for deuteros correction a color filter of transmission characteristic $\tau_D(\lambda)$ also shown would be necessary. The transmission characteristics $\tau_P(\lambda)$ and $\tau_D(\lambda)$ are obtained according to equations (4) and (5), respectively. For tritos no correction is necessary, and this corresponds to a horizontal transmission characteristic $\tau_T(\lambda)$.

The transmission characteristic $\tau(\lambda)$ of the color filter to be implemented, as shown by dotted line in FIG. 7, is generated so that the transmission characteristics $\tau_P(\lambda)$, $\tau_D(\lambda)$ and $\tau_T(\lambda)$ are chosen in the wavelength ranges from 548 to 780 nm, from 489 to 548 nm, and from 380 to 489 nm, respectively, and a continuous curve is approximated to these three sections. The color filter can be realized by applying optical layers of specified materials and thicknesses on a carrier by means of any thin-layer technology. To obtain the transmission characteristic $\tau(\lambda)$ as shown, the following ten thin-layers are applied in sequence on a transparent plastic carrier.

| Layer 1 | 0.25 $\mu$m | $MgF_2$ |
|---------|-------------|---------|
| Layer 2 | 0.95 $\mu$m | $ZrO_2$ + $TiO_2$ compound |
| Layer 3 | 0.25 $\mu$m | $MgF_2$ |
| Layer 4 | 0.25 $\mu$m | $ZrO_2$ + $TiO_2$ compound |

-continued

| Layer 5 | 0.25 μm | MgF$_2$ |
| Layer 6 | 0.25 μm | ZrO$_2$ + TiO$_2$ compound |
| Layer 7 | 0.25 μm | SiO$_2$ |
| Layer 8 | 0.25 μm | ZrO$_2$ |
| Layer 9 | 0.40 μm | SiO$_2$ |
| Layer 10 | 0.50 μm | MgF$_2$ |

The compound ZrO$_2$+TiO$_2$ is a product manufactured under Code No. 16413 by the firm MERCK. It is advisable to apply a per se known UV-protecting layer as an eleventh layer. As a carrier e.g. a −2D eye-glass is used, if the person wears such eye-glass on his tested eye. If he does not wear glasses, the layers are applied on a OD eye-glass.

EXAMPLE 3

Figure 8:
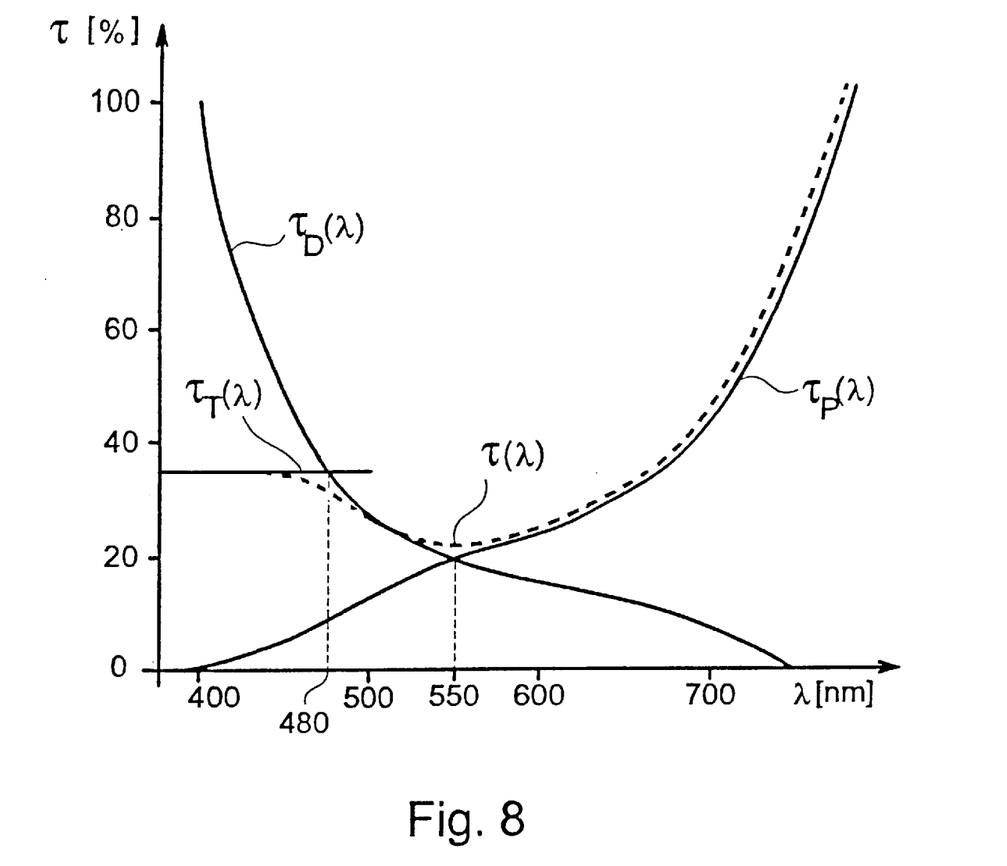

By testing a given person's eye, it has been determined that the sensitivity curve of the protos was displaced by 12.5 nm towards smaller wavelengths, the sensitivity curve of the deuteros was displaced by 7.5 nm towards greater wavelength and the tritos receptors had a sensitivity corresponding to that of a normal eye. The maxima of sensitivity curves P*($\lambda$) and D*($\lambda$) are 20 nm closer to each other than in the case of normal color vision. This means that $\Delta\lambda_P$=−12.5 nm, $\Delta\lambda_D$=7.5 nm and $\Delta\lambda_T$=0. For protos correction a color filter of the transmission characteristic $\tau_P(\lambda)$ as shown in FIG. 8 would be necessary, while for deuteros correction a color filter of transmission characteristic $\tau_D(\lambda)$ also shown would be required. For tritos no correction is necessary, and this corresponds to a horizontal transmission characteristic $\tau_T(\lambda)$. By generating the resultant of these three transmission characteristics, as described in Example 1, the transmission characteristic $\tau(\lambda)$ of the color filter to be implemented is obtained, as shown by dotted line in FIG. 8. The color filter can be realized by applying optical layers of specified materials and thicknesses on a carrier by means of any thin-layer technology. To obtain the transmission characteristic $\tau(\lambda)$ as shown, the following eight thin-layers are applied in sequence on a glass carrier.

| Layer 1 | 0.46 μm | ZrO$_2$ |
| Layer 2 | 0.05 μm | SiO$_2$ |
| Layer 3 | 0.05 μm | ZrO$_2$ |
| Layer 4 | 0.18 μm | SiO$_2$ |
| Layer 5 | 0.26 μm | ZrO$_2$ |
| Layer 6 | 0.28 μm | SiO$_2$ |
| Layer 7 | 1.74 μm | ZrO$_2$ |
| Layer 8 | 0.25 μm | MgF$_2$ |

Figures 15, 16, 17:
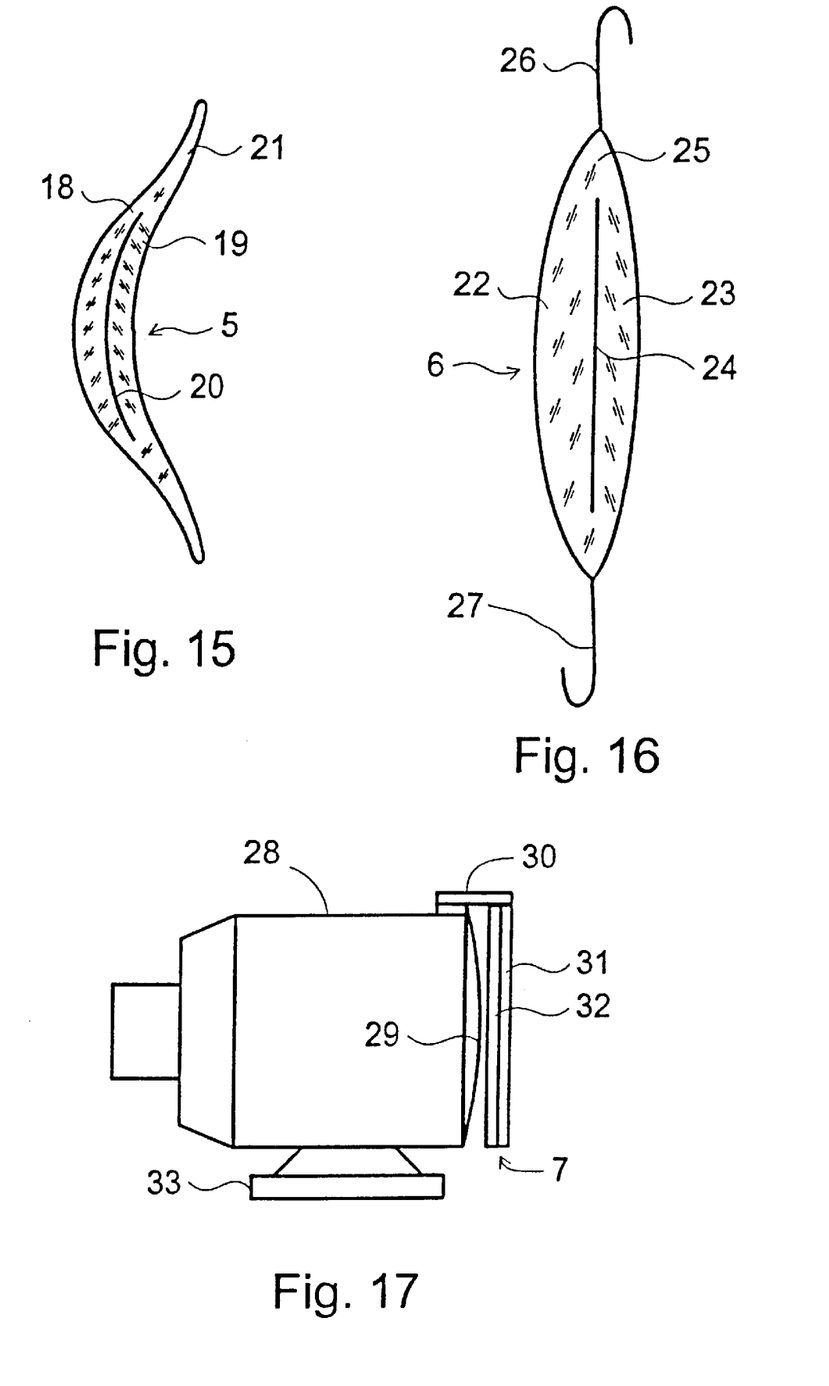
FIG. 15 is a schematic cross section of an embodiment of the optical means according to the invention formed as a contact lens.
FIG. 16 is a schematic cross section of an embodiment of the optical means according to the invention formed as an intraocular lens.
FIG. 17 is a schematic side view of an embodiment of the optical means according to the invention formed as a filter plate for color TV set.

As a ninth layer, a UV-protecting layer per se known can be applied. As a carrier, e.g. a hard +5D contact lens is used in a way that the thin-layers are hermetically sealed between two plastic half-lenses. The thin-layers are applied on one of the half-lenses and then the two half-lenses are put together and melted along their edges (FIG. 15).

EXAMPLE 4

Figure 9:
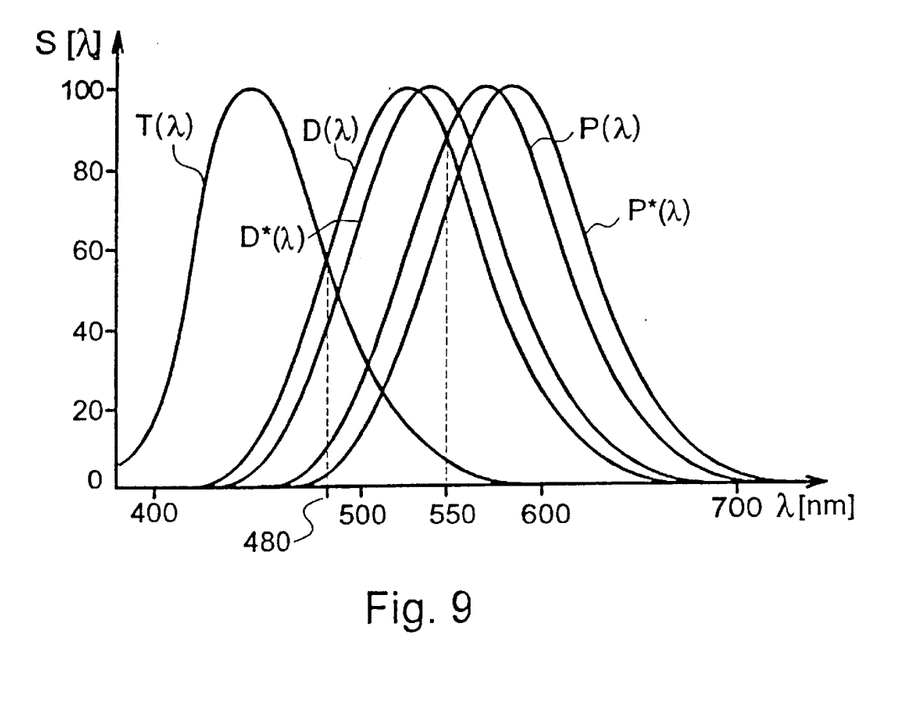
FIG. 9 is a diagram depicting spectral sensitivity curves of color sensitive receptors in a normal human eye and those in a human eye exhibiting another type of color vision anomaly.
Figure 10:
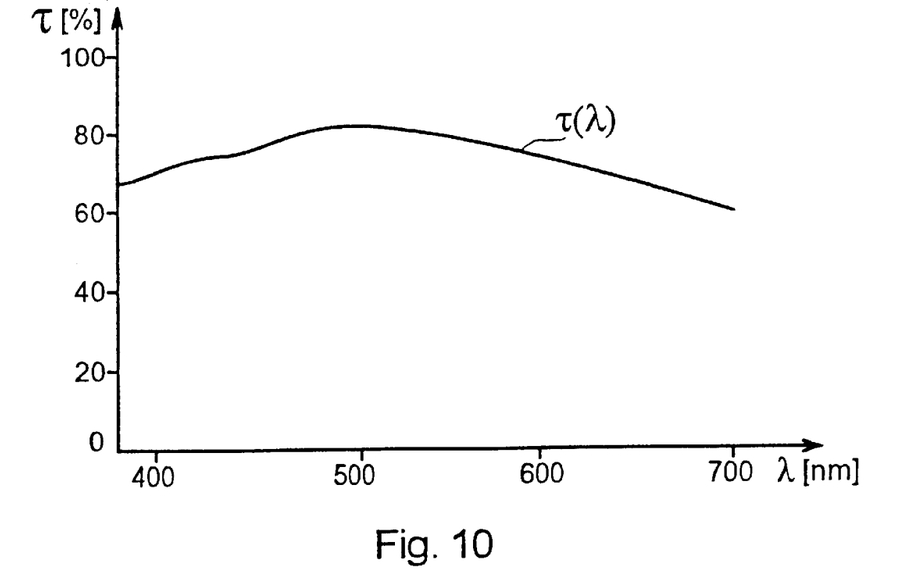
FIG. 10 is a diagram showing spectral transmission characteristic of a color filter according to the invention for improving the color vision of an eye exhibiting the anomaly as of FIG. 9, FIGS. 11 to 14 are schematic cross sections of different embodiments of the optical means according to the invention formed as eye-glasses.

By testing a given person's eye, it has been determined that the sensitivity curves of the protos and deuteros were displaced towards greater wavelengths by 10 nm each, while the tritos receptors were of a sensitivity corresponding to that of a normal eye. This means that $\Delta\lambda_P$=10 nm, $\Delta\lambda_D$=10 nm and $\Delta\lambda_T$=0. FIG. 9 shows the sensitivity curves P($\lambda$), D($\lambda$), T($\lambda$) of receptors in a normal human eye and also the sensitivity curves P*($\lambda$), D*($\lambda$) and T*($\lambda$) of the receptors of the eye exhibiting the anomaly as above. For the correction of the anomaly a color filter of a transmission characteristic $\tau(\lambda)$ as shown in FIG. 10 is suitable, which can be implemented by means of a 2 mm thick glass filter made of a colored glass manufactured by the firm BALZERS under Code No. 8006T240.

The optical means for improving or modifying color vision comprising a color filter of transmission $\tau(\lambda)$ can be made as conventional eye-glasses, in the form of contact lens or intraocular lens, or as any other optical means placed between the eye and the object to be viewed. The eye-glasses could be similar to simple sunglasses, but for people who wear glasses anyway to correct dioptric errors, a coating of optical thin-layers or a painting, forming a color filter according to the invention, can be applied on dioptric glasses. Hereinafter, some embodiments of the optical means for improving or modifying color vision according to the invention will be described on the basis of drawings.

Figure 11:
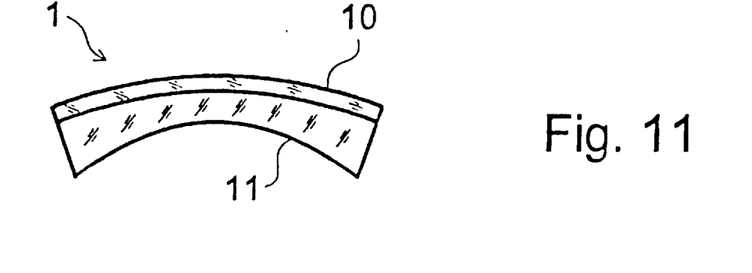

FIG. 11 shows optical means implemented as an eye-glass 1 comprising a negative dioptric lens 11 and a zero-diopter colored lens 10, which lens 10 forms a color filter according to the invention. It is advisable to match the lens 10 to the standard curvature surface of the dioptric lens 11. The material of the lenses 10 and 11 could be glass or plastic.

Figure 12:
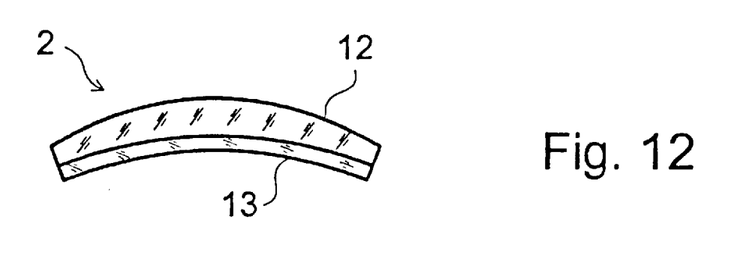

FIG. 12 shows optical means implemented as an eye-glass 2 comprising a positive dioptric lens 12 and a zero-diopter colored lens 13, the latter representing a color filter according to the invention. Again, the lens 13 is matched to the standard curvature surface of the dioptric lens 12. The material of the lenses 12 and 13 could be glass or plastic.

Figure 13:
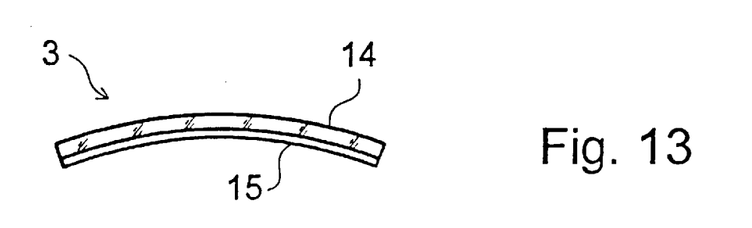

FIG. 13 shows optical means implemented as an eye-glass 3 comprising a zero-diopter glass or plastic lens 14 and optical thin-layers 15 applied on its concave surface. The thin-layers 15 represent an interference color filter according to the invention. The optical thin-layers 15 are shown in the drawing, for sake of visibility, much thinner than their real thickness.

Figure 14:
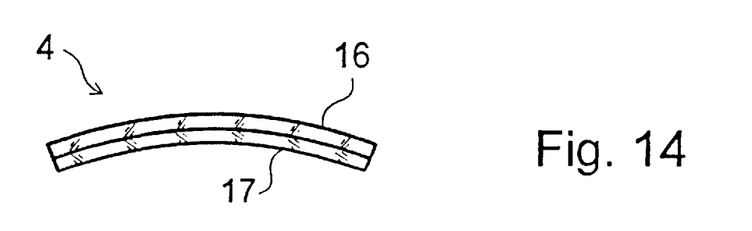

FIG. 14 shows optical means implemented as an eyeglass 4 comprising zero-diopter colored lenses 16 and 17, which together represent a color filter according to the invention. The material of the lenses 16 and 17 could be glass or plastic.

FIG. 15 shows optical means implemented as a contact lens 5 comprising two half-lenses 18 and 19 of hard material, which assure the necessary diopters, and between them optical thin-layers 20 to make up an interference color filter according to the invention. The thin-layers 20 are applied on one of the half-lenses, e.g. on the half-lens 18, and then the two half-lenses 18 and 19 are put together and melted along their edges 21. The biocompatible material of the half-lenses 18 and 19 hermetically seals the thin-layers 20, so they cannot cause any problem when wearing the contact lens 5. In some cases, the contact lens 5 may also be made of colored plastic material of appropriate transmission characteristic, these contact lenses 5 may also be made of a soft material.

FIG. 16 shows optical means implemented as an intraocular lens 6, which is to replace the natural lens of the eye mostly in the course of cataract operation. Between two half-lenses 22 and 23, which assure the necessary dioptres, there are optical thin-layers 24 to make up the colour filter according to the invention. The thin-layers 24 are applied on one of the half-lenses, e.g. on the half-lens 22, and then the two half-lenses 22 and 23 are put together and melted along their edges 25. The biocompatible material of the half-lenses 22 and 23 hermetically seals the thin-layers 24, so they cannot cause any problem when wearing the implanted intraocular lens 6. The intraocular lens 6 has two hapticas 26 and 27, per se known, for fixing the intraocular lens 6.

FIG. 17 shows optical means implemented as a filter plate 7, which can be placed in front of a screen 29 of a color TV set 28 having a support 33, or of a color display, by means of a per se known suspending structure 30. If a person with anomalous color vision would like to watch a TV screen 29 in realistic colors, he puts on the filter plate 7. The filter plate 7 as shown comprises two glass or transparent plastic layers 31 and 32 with different coloring, but it can be made of a plate of glass or transparent plastic material on which an interference filter representing the color filter according to the invention is applied. However, the filter plate 7 may also be implemented in any other way already mentioned. It is also possible to apply, e.g. by vaporization, an optical thin-layer system representing the color filter according to the invention on the screen 29.

According to the invention, not only anomalous color vision can be corrected, but a normal color vision can also be modified, e.g. the color distinguishing ability of a person with normal color vision may be improved in order to execute a special task easier. E.g. the red-green color distinguishing ability can be improved by virtually shifting the sensitivity curve $P^*(\lambda)$ in the wavelength range around the maximum value of sensitivity curve $P(\lambda)$ towards greater wavelengths and the sensitivity curve $D^*(\lambda)$ in the wavelength range around the maximum value of sensitivity curve $D(\lambda)$ towards smaller wavelengths. This possibility can be applied e.g. in medical diagnosis in dermatology, in visual tasks of image processing, in quality testing of foodstuff, in sorting tasks, in special military tasks, in forgery tests of banknotes. The optical means according to the invention can be implemented so that for a person having normal color vision, the modification of the color vision for a special task is accomplished for one of his eye, only. In order to achieve a desired color vision, transmission characteristic $\tau(\lambda)$ of the color filter according to the invention can be determined on the basis of equations (4) to (6) in a way that instead of the sensitivity curves of receptors of a normal eye, sensitivity curves corresponding to the desired color vision are taken into consideration.

According to the invention, the color filter of the optical means to improve or modify color vision is to be determined on the basis of color vision characteristics of the given eye. In general, both eyes of a person of anomalous color vision exhibit the same anomalous color vision. Rarely, there are individuals with different color vision in both eyes, which means that, of course, each eye needs a color filter of its own to correct its parachromatism, different from the color filter of the other eye.

It will be evident to those skilled in the art that the above disclosures are exemplary only and that various other alternatives, adaptations and modifications may be made within the scope of the present invention as defined by the following claims.

We claim:

1. A method for modifying color vision of an eye, comprising the steps of:
   determining spectral sensitivity curves of color-sensitive receptors of said eye with color vision to be modified; and
   applying a color filter with a spectral transmission selected to correct, in at least one of three wavelength ranges in a vicinity of maximum values of the spectral sensitivity curves of the color-sensitive receptors, wavelength shifts and shape deformations of said spectral sensitivity curves along a wavelength axis, as determined, so as to correspond to spectral sensitivity curves of receptors of an eye with normal or desired color vision and wherein the spectral sensitivity curves of the color-sensitive receptors of aid eye with color vision to be modified are shifted along the wavelength axis independently of each other.

2. The method according to claim 1, wherein said spectral transmission of said color filter is obtained by generating three quotient curves from spectral sensitivity curves of protos, deuteros and tritos receptors of a human eye with normal or desired color vision and said spectral sensitivity curves, as determined, of corresponding receptors of said eye with color vision to be modified, and choosing said spectral transmission in each of said three wavelength ranges substantially according to said respective quotient curve.

3. The method according to claim 2, wherein said spectral transmission of said color filter is determined by matching a continuous curve to said three quotient curves and transforming said continuous curve by multiplying by a constant so that its normalized maximum value is greater than 90%.

4. The method according to claim 2, wherein said spectral transmission of said color filter is determined by matching said three quotient curves to one another at boundaries of said three wavelength ranges by multiplying said quotient curves by constants in order to obtain a continuous curve and transforming said continuous curve by multiplying by a constant so that its normalized maximum value is greater than 90%.

5. The method according to claim 1, further characterized by providing a set of color filters representing a two- or three-dimensional multitude, the color filters of said set compensate displacements of different wavelength values of spectral sensitivity curves in one or two or three of said wavelength ranges, and applying that color filter of said set which compensate displacements the values of which are the nearest to said displacements of said spectral sensitivity curves as determined.

6. The method according to claim 1, wherein said three wavelength ranges are a first wavelength range extending from 550±30 nm to 780 nm, a second wavelength range extending from 480±20 nm to 550±30 nm, and a third wavelength range extending from 380 nm to 480±20 nm.

7. Optical means for modifying color vision of an eye, comprising a color filter having a spectral transmission selected to correct, in at least one of three wavelength ranges in a vicinity of maximum values of spectral sensitivity curves of color-sensitive receptors of an eye, wavelength shifts and shape deformations of spectral sensitivity curves along a wavelength axis, as determined, of said eye with color vision to be modified so as to correspond to spectral sensitivity curves of receptors of an eye with normal or desired color vision and wherein the spectral sensitivity curves of the color-sensitive receptors of said eye with color vision to be modified are shifted along the wavelength axis independently of each other.

8. The optical means according to claim 7, wherein said spectral transmission of said color filter substantially corresponds in said three wavelength ranges to three curves obtained as quotients of spectral sensitivity curves of protos, deuteros and tritos receptors of a human eye with normal or desired color vision and said spectral sensitivity curves, as determined, of corresponding receptors of said eye with color vision to be modified.

9. The optical means according to claim 7, wherein said color filter has a spectral transmission the values of which are, in each of said three wavelength ranges, monotonously increasing, or monotonously decreasing, or substantially constant, there being at least one of said three wavelength ranges in which the spectral transmission is monotonously increasing or decreasing.

10. The optical means according to claim 7, wherein said spectral transmission of said color filter has a normalized maximum value which is greater than 90%.

11. The optical means according to claim 7, wherein said optical means are a dioptric or zero-diopter eyeglass with at least one of an additive in a material of the eyeglass, an additive painted on a surface of the eyeglass, at least two differently colored layers, and having a set of optical thin-layers on the surface of the eyeglass forming an interference filter.

12. The optical means according to claim 7, wherein said optical means are a dioptric or zero-diopter contact lens with at least one of an additive in a material of the contact lens, an additive painted on a surface of the contact lens, at least two differently colored layers, and comprising a set of optical thin-layers forming an interference filter.

13. The optical means according to claim 12, wherein said set of optical thin-layers are hermetically sealed into the material of said lens.

14. The optical means according to claim 7, wherein said optical means are a dioptric or zero-diopter intraocular lens with at least one of an additive in a material of the intraocular lens, an additive painted on a surface of the intraocular lens, at least two differently colored layers, and comprising a set of optical thin-layers forming an interference filter.

15. The optical means according to claim 14, wherein said set of optical thin-layers are hermetically sealed into the material of said lens.

16. The optical means according to claim 7, wherein said optical means include a glass or transparent plastic filter plate with at least one of an additive in a material of the glass or transparent plastic filter plate an additive painted on a surface of the glass or transparent plastic filter plate, at least two differently colored layers, and a set of optical thin-layers forming an interference filter.

17. The optical means according to claim 7, further comprising a layer protecting against UV radiation.

18. The optical means according to claim 7, wherein said three wavelength ranges are a first wavelength range extending from 550±30 nm to 780 nm, a second wavelength range extending from 480±20 nm to 550±30 nm, and a third wavelength range extending from 380 nm to 480±20 nm.

19. A method for modifying color vision of an eye, comprising the steps of:
determining wavelength values associated with maxima of spectral sensitivity curves of color-sensitive receptors of said eye with color vision to be modified; and
applying a color filter with a spectral transmission selected to correct, in at least one of three wavelength ranges in a vicinity of maximum values of the spectral sensitivity curves of color-sensitive receptors, wavelength shifts of said maxima and shape deformations of the spectral sensitivity curves along a wavelength axis, as determined, so as to correspond to spectral sensitivity curves of receptors of an eye with normal or desired color vision and wherein the spectral sensitivity curves of the color-sensitive receptors of said eye with color vision to be modified are shifted along the wavelength axis independently of each other.

20. The method according to claim 19, wherein said spectral transmission of said color filter is obtained by generating three quotient curves from spectral sensitivity curves of protos, deuteros and tritos receptors of a human eye with normal or desired color vision and curves obtained by shifting along the wavelength maxima of these spectral sensitivity curves to maxima, as determined, of said spectral sensitivity curves of corresponding receptors of said eye with color vision to be modified, and choosing said spectral transmission in each of said three wavelength ranges substantially according to said respective quotient curve.

21. The method according to claim 20, wherein said spectral transmission of said color filter is determined by matching a continuous curve to said three quotient curves and transforming said continuous curve by multiplying by a constant so that its normalized maximum value is greater than 90%.

22. The method according to claim 20, wherein said spectral transmission of said color filter is determined by matching said three quotient curves to one another at boundaries of said three wavelength ranges by multiplying said quotient curves by constants in order to obtain a continuous curve and transforming said continuous curve by multiplying by a constant so that its normalized maximum value is greater than 90%.

23. A method of correcting color vision of an eye, comprising the steps of:
determining wavelength shifts and shape deformations of the spectral sensitivity curves of protos, deuteros, and tritos receptors of the eye to be corrected compared to corresponding spectral sensitivity curves of an eye with normal color vision;
selecting a spectral transmission by generating quotient curves from the spectral sensitivity curves of the eye to be corrected and the spectral sensitivity curves of the eye with normal color vision;
placing a color filter in a light path to the eye to be corrected, the color filter having the selected spectral transmission to correct the wavelength shifts and the shape deformations, thereby correcting the color vision of the eye and wherein the spectral sensitivity curves of the protos, deuteros, and tritos receptors of the eye to be corrected are shifted along a wavelength axis independently of each other.

* * * * *

UNITED STATES PATENT AND TRADEMARK OFFICE
CERTIFICATE OF CORRECTION

PATENT NO. : 5,774,202
DATED : June 30, 1998
INVENTOR(S) : Gyorgy ABRAHAM et al.

It is certified that error appears in the above-indentified patent and that said Letters Patent is hereby corrected as shown below:

On the title page, Item [75], change the name of the second inventor from "Guttfriedné Wenzel" to --Gottfriedné Wenzel--.

Column 15, line 13, (claim 11, line 5), cancel "having".

Column 15, line 20, (claim 12, line 5), cancel "comprising".

Column 15, line 29, (claim 14, line 5), cancel "comprising".

Signed and Sealed this

Twelfth Day of January, 1999

*Attest:*

*Attesting Officer*    *Acting Commissioner of Patents and Trademarks*